US009271895B2

(12) United States Patent
Mor et al.

(10) Patent No.: US 9,271,895 B2
(45) Date of Patent: Mar. 1, 2016

(54) METHOD FOR TREATING URINARY INCONTINENCE

(75) Inventors: Amit Mor, Rehovot (IL); Avi Elbaz, Dimona (IL)

(73) Assignee: APOS—Medical and Sports Technologies Ltd., Herzliya (IL)

( * ) Notice: Subject to any disclaimer, the term of this patent is extended or adjusted under 35 U.S.C. 154(b) by 210 days.

(21) Appl. No.: 13/810,498

(22) PCT Filed: Jul. 21, 2011

(86) PCT No.: PCT/IL2011/000583
§ 371 (c)(1), (2), (4) Date: Jan. 16, 2013

(87) PCT Pub. No.: WO2012/011109
PCT Pub. Date: Jan. 26, 2012

(65) Prior Publication Data

US 2013/0116726 A1 May 9, 2013

Related U.S. Application Data

(60) Provisional application No. 61/366,189, filed on Jul. 21, 2010.

(51) Int. Cl.
*A61B 17/00* (2006.01)
*A61H 39/04* (2006.01)
(Continued)

(52) U.S. Cl.
CPC ................ *A61H 39/04* (2013.01); *A43B 3/163* (2013.01); *A43B 7/144* (2013.01); *A43B 7/146* (2013.01); *A43B 7/147* (2013.01); *A43B 7/1445* (2013.01); *A43B 13/145* (2013.01); *A63B 21/0004* (2013.01); *A63B 21/4015* (2015.10); *A63B 22/18* (2013.01); *A63B 26/003* (2013.01); *A63B 23/08* (2013.01); *A63B 23/20* (2013.01); *A63B 2022/185* (2013.01); *A63B 2208/0204* (2013.01); *A63B 2209/10* (2013.01)

(58) Field of Classification Search
CPC ...... A61H 39/04; A63B 21/143; A63B 23/08; A63B 2208/0204; A63B 2022/185; A63B 26/003; A63B 23/20; A43B 7/144; A43B 7/146; A43B 7/147; A43B 7/1445; A43B 3/163; A43B 13/145
See application file for complete search history.

(56) References Cited

U.S. PATENT DOCUMENTS

| | | | |
|---|---|---|---|
| 1,021,142 A | 3/1912 | Freeman |
| 2004/0111925 A1 | 6/2004 | Fukui |
| 2004/0181969 A1 | 9/2004 | Smaldone |
| 2007/0289170 A1 | 12/2007 | Avent |

FOREIGN PATENT DOCUMENTS

JP 2007029700 A 2/2007

OTHER PUBLICATIONS

International Search Report from the US patent office in a counterpart PCT application—1 page, mailed Junayar 9, 2012.

(Continued)

*Primary Examiner* — Ashley Fishback
(74) *Attorney, Agent, or Firm* — Roach Brown McCarthy & Gruber, P.C.; Kevin D. McCarthy

(57) ABSTRACT

A method of treating urinary incontinence, uncontrolled urination, and frequent urination in a human in need thereof is provided. The method includes placement of at least two calibrated, differential disturbances or protuberances under the human's feet.

20 Claims, 11 Drawing Sheets

(51) Int. Cl.

| | |
|---|---|
| ***A43B 13/14*** | (2006.01) |
| ***A43B 7/14*** | (2006.01) |
| ***A63B 21/00*** | (2006.01) |
| ***A63B 22/18*** | (2006.01) |
| ***A63B 26/00*** | (2006.01) |
| ***A43B 3/16*** | (2006.01) |
| *A63B 23/08* | (2006.01) |
| *A63B 23/20* | (2006.01) |

(56) References Cited

OTHER PUBLICATIONS

ISR of corresponding PCT application—mailed Jan. 9, 2012, 3 pages.

The Effect of Ankle Inclination in Upright Position on the Electromyographic Activity of Pelvic Floor Muscles in Women with Stress Urinary Incontinence (Cerruto et al) Jan. 24, 2008, European Urology, vol. 53, Issue 5, pp. 1094-1095. DOI: 10.1016/j.eurouro.2008.01.046.

METHOD FOR TREATING URINARY INCONTINENCE

FIELD OF INVENTION

This invention is directed, inter alia, to methods for treating urinary incontinence or frequent urination in a subject in need thereof.

BACKGROUND OF THE INVENTION

Urinary incontinence or the loss of bladder control is a common and often embarrassing problem. The severity of urinary incontinence ranges from occasionally leaking urine when one coughs or sneezes to having an urge to urinate that is so sudden and strong one does not get to a toilet in time.

The three main types of urinary incontinence are: stress incontinence: occurs during certain activities like coughing, sneezing, laughing, or exercise; urge incontinence: involves a strong, sudden need to urinate followed by instant bladder contraction and involuntary loss of urine; and overflow incontinence: occurs when the bladder cannot empty completely, which leads to dribbling.

Incontinence is most common among the elderly. Women are more likely than men to have urinary incontinence. Infants and children are not considered incontinent, but merely untrained, up to the time of toilet training. Occasional accidents are not unusual in children up to age 6 years. Young (and sometimes teenage) girls may have slight leakage of urine when laughing. Nighttime urination in children is normal until the age of 5 or 6.

Normally, the bladder begins to fill with urine from the kidneys. The bladder stretches to allow increasing amounts of urine. The first urge to urinate occurs when around 200 mL of urine is stored in the bladder. A healthy nervous system will respond to this stretching sensation by alerting the urge to urinate, while also allowing the bladder to continue to fill. The average person can hold around 350 to 550 mL of urine. Two muscles help control the flow of urine: the sphincter must be able to squeeze to prevent urine from leaking. The bladder wall muscle (detrusor) must stay relaxed so the bladder can expand. When it is time to empty the bladder, the bladder wall (detrusor) muscle contracts or squeezes to force urine out of the bladder. Before this muscle squeezes, the body must be able to relax the sphincter to allow the urine to pass out of the body.

The ability to control urination depends on having normal anatomy, a normally functioning nervous system, and the ability to recognize and respond to the urge to urinate.

SUMMARY OF THE INVENTION

In one embodiment, the present invention provides a method of treating a subject suffering from urinary incontinence comprising the steps of: (a) securing a device to a subject's foot, whereby the device comprises a foot securing mean, a support member operably attached to said securing mean, and a moveable anterior protuberance and a moveable posterior protuberance, wherein the anterior protuberance and the posterior protuberance are ground engaging; (b) calibrating the posterior protuberance and the anterior protuberance to: (1) a balanced position, wherein the balanced position comprises a position whereby the device provides a reduced inversion, a reduced eversion, or both to the subject's foot during the stance phases; and (2) balanced timing of heel rise; and (c) fixing said posterior protuberance and the anterior protuberance to the support member.

In another embodiment, the present invention provides a method of reducing urinary urgency, high urinary frequency or a combination thereof in a subject in need thereof comprising the steps of: (a) securing a device to a subject's foot, whereby the device comprises a foot securing mean, a support member operably attached to said securing mean, and a moveable anterior protuberance and a moveable posterior protuberance, wherein the anterior protuberance and the posterior protuberance are ground engaging; (b) calibrating the posterior protuberance and the anterior protuberance to: (1) a balanced position, wherein the balanced position comprises a position whereby the device provides a reduced inversion, a reduced eversion, or both to the subject's foot during the stance phases; and (2) balanced timing of heel rise; and (c) fixing said posterior protuberance and the anterior protuberance to the support member.

BRIEF DESCRIPTION OF THE DRAWINGS

The present invention will be understood and appreciated more fully from the following detailed description taken in conjunction with the appended drawings in which.

DETAILED DESCRIPTION OF THE INVENTION

This invention provides, in one embodiment, a method of treating a subject suffering from urinary incontinence comprising the steps of: (a) securing a device to a subject's foot, whereby the device comprises a foot securing mean, a support member operably attached to said securing mean, and a moveable anterior protuberance and a moveable posterior protuberance, wherein the anterior protuberance and the posterior protuberance are ground engaging; (b) calibrating the posterior protuberance and the anterior protuberance to: (1) a balanced position, wherein the balanced position comprises a position whereby the device provides a reduced inversion, a reduced eversion, or both to the subject's foot during the stance phases; and (2) balanced timing of heel rise; and (c) fixing said posterior protuberance and the anterior protuberance to the support member.

In another embodiment, the present invention provides a method of reducing urinary urgency, high urinary frequency or a combination thereof in a subject in need thereof comprising the steps of: (a) securing a device to a subject's foot, whereby the device comprises a foot securing mean, a support member operably attached to said securing mean, and a moveable anterior protuberance and a moveable posterior protuberance, wherein the anterior protuberance and the posterior protuberance are ground engaging; (b) calibrating the posterior protuberance and the anterior protuberance to: (1) a balanced position, wherein the balanced position comprises a position whereby the device provides a reduced inversion, a reduced eversion, or both to the subject's foot during the stance phases; and (2) balanced timing of heel rise; and (c) fixing said posterior protuberance and the anterior protuberance to the support member. In another embodiment, securing is fastening or adapting.

In another embodiment, stance phases comprise initial contact of foot with ground, loading bodyweight onto the stance leg (loading response), mid-stance, heel off, and push off.

Figure 1:
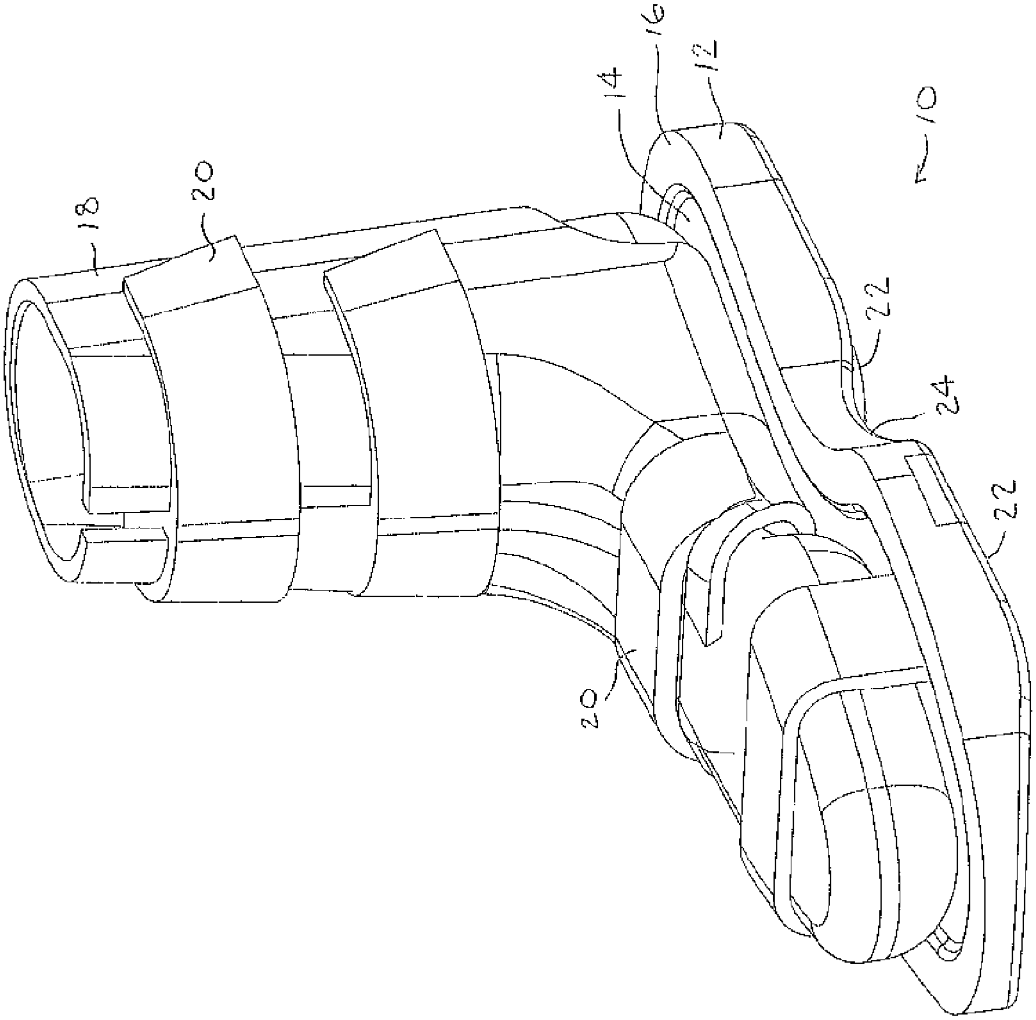
FIG. 1 is a simplified pictorial illustration of footwear constructed and operative in accordance with an embodiment of the present invention.

In another embodiment, balancing timing of heel rise comprises correcting instances wherein the heel is pulled off the ground earlier than normal-early-heel rise. In another embodiment, the typical pattern is a whipping motion upwards and medial. In another embodiment, correction comprises lifting a posterior protuberance thus bringing an ankle towards a plantar flexed position. This is done, in some embodiments, by the insertion of a 0.5-8 mm spacer between the protuberance and the lower surface (element 24 in FIG. 1 or 2) or outsole, thus bringing the ankle towards a plantar flexed position. In another embodiment, lifting a protuberance is increasing the height of a protuberance.

In another embodiment, balancing timing of heel rise comprises correcting instances termed late-heel rise. In another embodiment, late-heel rise is observed as a wobbling medial and lateral rocking motion of the foot. In another embodiment, correction comprises lifting an anterior protuberance thus bringing an ankle towards a slightly more dorsi-flexed position. This is done, in some embodiments, by the insertion of a 0.5-8 mm spacer between the protuberance and the lower surface 24 (element 24 in FIG. 1 or 2) or outsole, thus bringing the ankle towards a slightly more dorsi-flexed position.

In another embodiment, provided herein that methods as described herein further alleviate bladder or prostate pain. In another embodiment, provided herein that treating the indications provided herein comprises alleviating bladder or prostate related pain.

In another embodiment, the methods disclosed herein are directed to methods of improving the control over urinary secretion. In another embodiment, the methods disclosed herein are based on the unexpected discovery that by changing the center of pressure (COP) with which the foot contacts the ground urinary incontinence can be treated and even cured. In another embodiment, changing the center of pressure (COP) with which the foot contacts the ground is executed through calibrating the device (footwear) of the invention. In another embodiment, COP is changed or altered via a perturbation induced by a protuberance as disclosed herein. In another embodiment, a device of the invention alters COP thus changing the movement pattern of a lower limb. In another embodiment, the methods of the invention provide a controlled change in movement pattern and concomitantly avoiding damage, injury, trauma, or a combination thereof (such as but not limited to: falls, damaging gait, damaging lower limb neuromuscular control or activity) to the subject using the device, thus efficiently enabling the accomplishment of the methods provided herein.

In another embodiment, methods of the present invention unexpectedly provide exercises to strengthen the pelvic floor muscles. In another embodiment, methods of the present invention unexpectedly are far more effective than Kegels and far less time consuming than Kegels. In another embodiment, methods of the present invention are suitable to any person that can walk. In another embodiment, methods of the present invention are suitable for any woman that can walk unlike Kegels exercises which are not suitable to many women that can't isolate the pelvic floor muscles by their own.

In another embodiment, the methods of the invention provide that the subject wearing the device performs activities such as: walking, standing, cooking or getting up from a chair with the device worn on both feet. In another embodiment, the device is footwear comprising at least two protuberances wherein only the protuberances are ground engaging during activities such: walking, standing, cooking or getting up from a chair with the device worn on both feet. In another embodiment, the device is footwear comprising at least two protuberances wherein predominantly the protuberances are ground engaging during activities such: walking, standing, cooking or getting up from a chair with the device worn on both feet.

In another embodiment, predominantly is over 60% of the ground engaging period. In another embodiment, predominantly is over 70% of the ground engaging period. In another embodiment, predominantly is over 80% of the ground engaging period. In another embodiment, predominantly is over 90% of the ground engaging period. In another embodiment, predominantly is over 95% of the ground engaging period.

In another embodiment, ground engaging period is the period (time) in seconds wherein any part of the footwear is in contact with a ground surface. In another embodiment, ground engaging period is the period (time) in second wherein any part of the footwear is in contact with a ground surface during gait and/or stance.

Target Populations

In another embodiment, a subject in need thereof is a subject suffering from a urinary incontinence. In another embodiment, a subject in need thereof is a subject suffering from a high urinary frequency. In another embodiment, a subject in need thereof is a subject suffering from urgent urination which is a sudden, compelling urge to urinate, along with discomfort in the bladder. In another embodiment, a subject in need thereof is a subject suffering from frequent need to urinate at night (nocturia).

In another embodiment, a subject suffering from urinary incontinence or frequent urination is a woman during menopause. In another embodiment, a subject suffering from urinary incontinence is a post-menopausal woman.

In another embodiment, a subject suffering from urinary incontinence or a high urinary frequency is a subject further afflicted with benign prostatic hyperplasia, congestive heart failure, cystocele, diabetes, diabetes insipidus, overactive bladder, prostate cancer, diabetes insipidus—central, diabetes insipidus—nephrogenic, diabetes mellitus (type 1 or type 2), excessive intake of a high solute load (such as mannitol therapy in the hospital, or use of radiocontrast materials for radiology procedures), salt wasting kidney diseases (such as Bartter's syndrome), excessive fluid intake, use of diuretics, interstitial cystitis, multiple sclerosis, Parkinson's disease, post kidney stones, urethral strictures, urinary tract infections, anatomical abnormalities, overactive bladder (also called urge incontinence, which can be result from infection, cystitis, bladder tumors, or neurogenic bladder), a psychological factor, stress incontinence (which may be related to pregnancy, estrogen deficiency or pelvic surgery), damage form prostate surgery, neurogenic bladder, atrophic urethritis, delirium, or any combination thereof.

In another embodiment, a subject in need thereof is a subject suffering from muscle atrophy. In another embodiment, a subject in need thereof is a subject suffering from cachexia. In another embodiment, a subject in need thereof is a subject suffering from AIDS. In another embodiment, a subject in need thereof is a subject suffering from a congestive heart disease.

In another embodiment, a subject in need of a therapy according to the methods disclosed herein suffers from weak pelvic floor muscles which fail to retain the urine in the bladder when intra-abdominal pressure rises (ex. cough, laugh etc.). In another embodiment, a subject in need of a therapy according to the methods disclosed herein suffers from urge incontinence or the inability to control urine passing when feeling the need to urinate. In another embodiment, a subject in need of a therapy according to the methods disclosed herein suffers from overflow incontinence. In another embodiment, overflow incontinence occurs when urine continues to pass long after the subject has finished urinating. In another embodiment, a subject in need of a therapy according to the methods disclosed herein suffers from mixed incontinence.

In another embodiment, a subject in need of a therapy according to the methods disclosed herein is a woman who suffers from urinary stress incontinence, urinary urge incontinence, mixed urinary incontinence, overflow urinary incontinence or a combination thereof.

In another embodiment, a subject in need of a therapy according to the methods disclosed herein is a woman who suffers from increased urinary urgency or increased urinary frequency. In another embodiment, a subject in need of a therapy according to the methods disclosed herein is a man who suffers from prostate related urinary problems such as increased urination frequency. In another embodiment, a subject in need of a therapy according to the methods disclosed herein is a woman who has given vaginal birth in the past, who frequently suffers from urinary incontinence and/or increased urinary urgency and/or increased urinary frequency.

In another embodiment, the methods described herein are preformed by calibration of an anterior protuberance, a posterior protuberance or both. In another embodiment, the methods described herein involve wearing the device and performing daily activities with it, such as walking, household chores etc.

In another embodiment, the posterior protuberance, the anterior protuberance or both are calibrated in both the left and the right footwear to a position in which reduced inversion and reduced eversion of the ankle is achieved. In another embodiment, the posterior protuberance, the anterior protuberance or both are calibrated in both the left and the right footwear to a position in which reduced inversion and reduced eversion of the foot is achieved. In another embodiment, the posterior protuberance, the anterior protuberance or both are then fixed and the subject is given a treatment plan which details the amount of time the device should be worn per day. The treatment plan also details how much time out of the total wearing time should be spent in weight bearing (i.e. on ones feet).

In another embodiment, calibrating a protuberance comprises calibrating convexity, calibrating height, calibrating weight, calibrating position, or any combination thereof comprises a self control urinary effect. In another embodiment, the methods as described herein reduce the frequency of urination. In another embodiment, the methods as described herein enhance the control over urination.

In another embodiment, high urinary frequency or frequent urination comprises urinating more than 10 times a day. In another embodiment, high urinary frequency or frequent urination comprises urinating more than 15 times a day. In another embodiment, high urinary frequency or frequent urination comprises urinating more than 20 times a day. In another embodiment, high urinary frequency or frequent urination comprises urinating more than 25 times a day. In another embodiment, high urinary frequency or frequent urination comprises urinating more than 30 times a day.

In another embodiment, high urinary frequency or frequent urination comprises urinating small amounts of urine more than 10 times a day. In another embodiment, high urinary frequency or frequent urination comprises urinating small amounts of urine more than 15 times a day. In another embodiment, high urinary frequency or frequent urination comprises urinating small amounts of urine more than 20 times a day. In another embodiment, high urinary frequency or frequent urination comprises urinating small amounts of urine more than 25 times a day. In another embodiment, high urinary frequency or frequent urination comprises urinating small amounts of urine more than 30 times a day.

In another embodiment, placement and calibration of a protuberance comprises the induction of a differential interference during gait or walking. In another embodiment, the term "interference" comprises disturbance, interruption, interposition, perturbation, obstruction, or any combination thereof. In another embodiment, the ability to fine-tune an induced interference under a foot of a subject enables minimizing inversion and eversion as described herein. In another embodiment the balanced position comprises a position whereby the device provides a reduced inversion, a reduced eversion, or both to the subject's feet during the stance phases.

In another embodiment, provided herein that the posterior protuberance is a bulbous protuberance. In another embodiment, provided herein that the anterior protuberance is a bulbous protuberance. In another embodiment, provided herein that both the posterior (P) protuberance and the anterior (A) protuberance are bulbous protuberances.

Treating

In another embodiment, the methods as described herein involve exercise with the device as described herein. In another embodiment, exercise is walking, running, dancing, jumping or any other form of gait movement. In another embodiment, treating is curing the indication provided herein (urinary incontinence, frequent urination). In another embodiment, treating is reducing the frequency or rate of urination in a subject suffering from frequent urination. In another embodiment, frequent urination is the need to urinate more than eight times a day or urinating at night more than once. In another embodiment, treating is reducing the frequency of small volume urination in a subject in need thereof. In another embodiment, treating is increasing the volume of small volume urination. In another embodiment, treating is reducing urine leaks in a subject in need thereof. In another embodiment, treating is reducing the sensitivity of the bladder to excitement. In another embodiment, treating is reducing the sensitivity of the bladder to shivering or vibration. In another embodiment, treating is reducing the sensitivity of the bladder to laughter. In another embodiment, treating is reducing the sensitivity of the bladder to an increase in intra-abdominal pressure such as but not limited to: lifting objects, squatting etc. In another embodiment, treating is reducing the sensitivity of the bladder to coughs or sneezes. In another embodiment, treating is reducing the frequency of uncontrolled urination. In another embodiment, treating is diminishing uncontrolled urination. In another embodiment, treating is gaining control over urination. In another embodiment, the term "frequent urination" is known to one of skill in the art. In another embodiment, the term "frequent urination" is determined according to the subject's age, health, and physical condition. In another embodiment, the term "small volume urination" is known to one of skill in the art. In another embodiment, the term "small volume urination" is determined according to the subject's age, health, and physical condition. In another embodiment, treating is a process wherein the subject's disease or condition is ameliorated.

In another embodiment, the methods as described herein further comprises a combination treatment comprising the use of the device as described herein and a proper medication. In another embodiment, one of skill in the art will readily diagnose and prescribe the proper medication to a subject suffering from a disease or a condition such as described herein.

In another embodiment, the outcome of treatment as provided herein is apparent immediately after the initial use of the device as described herein. In another embodiment, the outcome of treatment as provided herein is apparent after 10-1000000 meters of walking with the device as described herein. In another embodiment, the outcome of treatment as provided herein is apparent after 50-100000 meters of walking with the device as described herein. In another embodiment, the outcome of treatment as provided herein is apparent after 500-10000 meters of walking with the device as described herein. In another embodiment, the outcome of treatment as provided herein is apparent after 500-5000 meters of walking with the device as described herein. In another embodiment, the outcome of treatment as provided herein is apparent after 500-3000 meters of walking with the device as described herein.

In another embodiment, a device as disclosed herein has an immediate effect with regard to treating or treatment of a disease, a pathology, and/or pain as provided herein. In another embodiment, short term immediate effect is apparent after walking with the device for 1-5 days. In another embodiment, short term immediate effect is apparent after walking with the device for 30-600 minutes. In another embodiment, short term immediate effect is apparent after walking with the device for 1-10 hours (hrs). In another embodiment, short term immediate effect is apparent after walking with the device for 5-1000 hours (hrs). In another embodiment, short term immediate effect is apparent after walking with the device for 12-96 hours (hrs). In another embodiment, short term immediate effect is apparent after walking with the device for 1-10 days. In another embodiment, short term immediate effect is apparent after walking with the device for 7-21 days. In another embodiment, short term immediate effect is apparent walking with the device for 5-30 days.

In another embodiment, the effect is apparent after walking with the device for 1-2 months. In another embodiment, the effect is apparent after walking with the device for 1-24 months. In another embodiment, the effect is apparent after walking with the device for 2-6 months. In another embodiment, the effect is apparent after walking with the device for 4-10 months. In another embodiment, the effect is apparent after walking with the device for 6-48 months. In another embodiment, the effect is apparent in after walking with the device for 12-24 months. In another embodiment, the effect is apparent after walking with the device for 10-30 months.

In another embodiment, a device as described herein is prescribed to a subject according to the subject's physical condition. In another embodiment, a device as described herein is prescribed to a subject according to the subject's medical condition. In another embodiment, a device as described herein is prescribed to a subject according to the subject's medical history. In another embodiment, prescription includes directions of how to use the device. In another embodiment, prescription includes intensity of use, daily use, or daily distance directions.

In another embodiment, any prescription as described herein comprises increase in daily usage time as the subject's gait improves. In another embodiment, any prescription as described herein comprises increase in daily usage time as subject's incontinence/pain decreases. In another embodiment, any prescription as described herein comprises increase in daily usage time as subject's disease or condition as described herein, improves. In another embodiment, a prescription as described herein further comprises medicating the subject according to his or hers medical condition.

In another embodiment, a prescription as described herein further comprises adjustments of the device as subject's lower limb muscles are tuned or are off balance. In another embodiment, adjustments of the device comprise calibrating or positioning a protuberance as described herein.

The Device

In another embodiment, the device is secured to a subject's foot directly. In another embodiment, the term "secured to a subject's foot" comprises securing the device to any footwear such as but not limited to shoes, boots, etc that are secured to a subject's foot. In another embodiment, a foot securing means secures the device such as footwear as shown in the figures to a subject's foot. In another embodiment, various different feet securing means can be used. In another embodiment, a foot securing mean comprises a plurality of securing means. In another embodiment, a foot securing mean is a lace. In another embodiment, a foot securing mean comprises a Velcro fastener. In another embodiment, a foot securing mean comprises securing straps. In another embodiment, reference is made to FIGS. 1-4, which illustrate footwear 10 constructed and operative in accordance with an embodiment of the present invention.

In another embodiment, the device is footwear comprising a shoe structure which includes at least two calibrated, differential disturbances or protuberances under the patient feet. In another embodiment, the shoe structure serves as a platform for placing at least two calibrated, differential or identical disturbances or protuberances under the patient feet.

In another embodiment, the upper part of the shoe structure serves as fastening or securing means/platform, while the sole is a platform for placing at least two calibrated, differential disturbances or protuberances under the patient feet. In another embodiment, the outsole is a platform for placing at least two calibrated, differential or identical disturbances or protuberances under the patient feet.

In another embodiment, a support member is operably attached to the securing mean. In another embodiment, operably attached comprises sufficient attachment between the securing mean and the support member. In another embodiment, a support member comprises the sole. In another embodiment, a support member comprises the inner sole. In another embodiment, a support member comprises the outer sole. In another embodiment, a support member comprises the middle sole. In another embodiment, a support member comprises the upper (the part of the shoe that is on top of the foot). In another embodiment, the upper is operably attached to the securing mean (such as but not limited to laces). In another embodiment, the upper comprises straps or totally enclosing the foot. In another embodiment, the upper comprises straps that function as securing means (such as sandals).

In another embodiment, a device such as footwear 10 is supplied as one or more pairs of shoe-like devices, or alternatively, as just one of the shoe-like devices. In another embodiment, footwear 10 comprises a support member 12 having a periphery in a shape of a shoe sole comprising an upper surface 14. In the illustrated embodiment, the upper surface 14 is indented with a peripheral ridge 16, but it is appreciated that other configurations of upper surface 14 are within the scope of the invention. In another embodiment, footwear 10 is attached to a foot of a user by means of a boot 18 and/or fasteners 20, such as but not limited to, VELCRO straps, buckles, shoe laces, and the like. In another embodiment, footwear 10 is attached to a foot of a user by means of a shoe. In another embodiment, a shoe comprises a platform of a sneaker. In another embodiment, the term sneaker comprises a boot. In another embodiment, the term sneaker comprises a walking boot. In another embodiment, a shoe comprises a platform of a running shoe. In another embodiment, a shoe comprises a platform of an elegant shoe. In another embodiment, a shoe comprises a platform of a walking shoe or boot.

In another embodiment, a device such as but not limited to boot 18 is fashioned for attachment to the user's foot with or without fasteners 20. In another embodiment, fasteners 20 are used as foot securing means to attach footwear 10 to the user's foot without boot 18.

Protuberances

In another embodiment, the invention provides that the device such as footwear 10 comprises protuberances in a fixed position. In another embodiment, the invention provides that the device such as footwear 10 comprises protuberances having any shape known to one of skill in the art. In another embodiment, the invention provides that the device comprises at least two bulbous protuberances. In another embodiment, a protuberance is symmetrical. In another embodiment, a protuberance is asymmetrical In another embodiment, a protuberance comprises a shape of a: polygon, decagon, digon, dodecagon, nonagon, henagon hendecagon, heptagon, hexadecagon, hexagon icosagon, octagon, pentagon, triangle, Penrose tile, trapezium, isosceles, trapezium undecagon, quadrilateral, Lozenge, rhomboid, rectangle, square, rhombus, trapezoid, polydrafter, arbelos, circle, disc, circle, excircle, crescent, dome, ellipse, lune, oval, sphere, asteroid, or deltoid.

In another embodiment, each protuberance 22 has a curved outer contour 26. In another embodiment, each protuberance has a different curved outer contour. In another embodiment, each protuberance 22 has a convexity.

In another embodiment, a protuberance comprises a dome shape. In another embodiment, a protuberance as described herein comprises a dome shape which further comprises multiple different convexities. In another embodiment, each protuberance 22 comprises a different convexity. In another embodiment, each protuberance 22 comprises a different set of convexities. The cross-section of the contour 26, that is, either the cross-section taken with respect to a longitudinal axis 28 (FIG. 4) of support member 12 (corresponding to the shape seen in FIG. 2) or the cross-section taken with respect to a latitudinal axis 30 (FIG. 4) of support member 12 (corresponding to the shape seen in FIG. 3), or any other cross-section, may have any curvilinear shape.

In another embodiment, the contours 26 may have the shape of a conic section, that is, the shape of a circle, ellipse, parabola or hyperbola. The various cross-sections of the contours 26 of protuberance 22 may be shaped identically or differently. In another embodiment, the shape of a protuberance is defined by equal arches. In another embodiment, the shape of a protuberance is defined by a variety of arches of different radiuses which are tangent to each other. In another embodiment, the shape of a protuberance is symmetrical. In another embodiment, the shape of a protuberance is asymmetrical. In another embodiment, a protuberance is a bulbous protuberance.

In another embodiment, the invention provides that the device such as footwear 10 supports the foot of a subject only by the two protuberances when the two protuberances are placed on a ground surface. In another embodiment, the invention provides that the device such as footwear 10 supports the foot of a subject during stance only by the two protuberances when the two protuberances are placed on a ground surface. In another embodiment, the invention provides that during stance only the 2 ground engaging surfaces of the protuberances (such as the peak or the surface facing the ground) are in contact with a ground surface. In another embodiment, the invention provides that during stance only the ground engaging surface in each protuberance is in contact with a ground surface.

In another embodiment, at least two bulbous protuberances 22 protrude from a lower surface 24 of support member 12. In another embodiment, only two bulbous protuberances 22 protrude from a lower surface 24 of support member 12. In another embodiment, a lower surface of support member is an outsole. In another embodiment, only two bulbous protuberances 22 protrude from a lower surface 24 of support member 12.

In another embodiment, the ground engaging parts of the device are only the protuberances. In another embodiment, during all phases of gait including the stance phase the protuberances are the only parts of the device which are ground engaging. In another embodiment, during all phases of gait including the stance phase the protuberances 22 are the only parts of the device which are in direct contact with the ground.

In another embodiment, a protuberance as described herein is movable. In another embodiment, a protuberance as described herein is fixed. In another embodiment, a protuberance as described herein is mountable. In another embodiment, a protuberance as described herein is replaceable. In another embodiment, a protuberance as described herein is movable along the outer surface of the support member. In another embodiment, a protuberance as described herein is movable along the outer surface of the outsole. In another embodiment, a protuberance as described herein can be positioned within the outer surface of the support member.

In another embodiment, a protuberance as described herein is movable or translatable such as in a track (e.g., forwards, backwards, sideways or diagonally) and/or rotatable about its own or other axis, or a combination of such motions.

In another embodiment, a protuberance is movable within a predefined area. In another embodiment, a protuberance is movable within an area of 1 $cm^2$ to 18 $cm^2$. In another embodiment, a protuberance is movable within an area of 1 $cm^2$ to 6 $cm^2$. In another embodiment, a protuberance is movable within an area of 1 $cm^2$ to 4 $cm^2$. In another embodiment, a protuberance is movable within an area of 2 $cm^2$ to 8 $cm^2$. In another embodiment, a protuberance is movable within an area of 3 $cm^2$ to 6 $cm^2$. In another embodiment, a protuberance is movable within an area of 4 $cm^2$ to 10 $cm^2$. In another embodiment, a protuberance is movable within an area of 5 $cm^2$ to 18 $cm^2$. In another embodiment, a protuberance is movable within an area of 4 $cm^2$ to 12 $cm^2$.

In another embodiment, a predefined area is a circle. In another embodiment, a predefined area is a square. In another embodiment, a predefined area is an ellipse. In another embodiment, a predefined area is a rectangle. In another embodiment, a predefined area is quadrangular. In another embodiment, a predefined area comprises any shape known to one of skill in the art. In another embodiment, a predefined area is shapeless.

In another embodiment, a protuberance can be positioned anywhere on the support member. In another embodiment, a protuberance can be fixed anywhere on the support member. In another embodiment, a protuberance can be positioned and/or fixed anywhere within a predefined area. In another embodiment, the protuberance is hooked to a rail. In another embodiment, the protuberance is connected to a rail. In another embodiment, the protuberance is connected to a rail and is movable along the rail. In another embodiment, the protuberance is connected to a rail, is movable along the rail, and can be positioned and/or fixed anywhere along the rail.

In another embodiment, a protuberance is slidingly mounted on support member. In another embodiment, a protuberance is mounted on a track 36 (FIG. 2) formed in the lower surface 24 of support member 12, and is selectively positioned anywhere along the track and fastened and or fixed thereto. In another embodiment, track 36 extends along a portion of the shoe sole or all along the length of the shoe sole. Alternatively or additionally, the amount of protrusion of a protuberance is adjusted, such as by mounting protuberance with a threaded fastener 38 (FIG. 3) to support member 12 and tightening or releasing threaded fastener. In another embodiment, the term "fastening", "fixing" and "securing" are used interchangeably.

Figure 3:
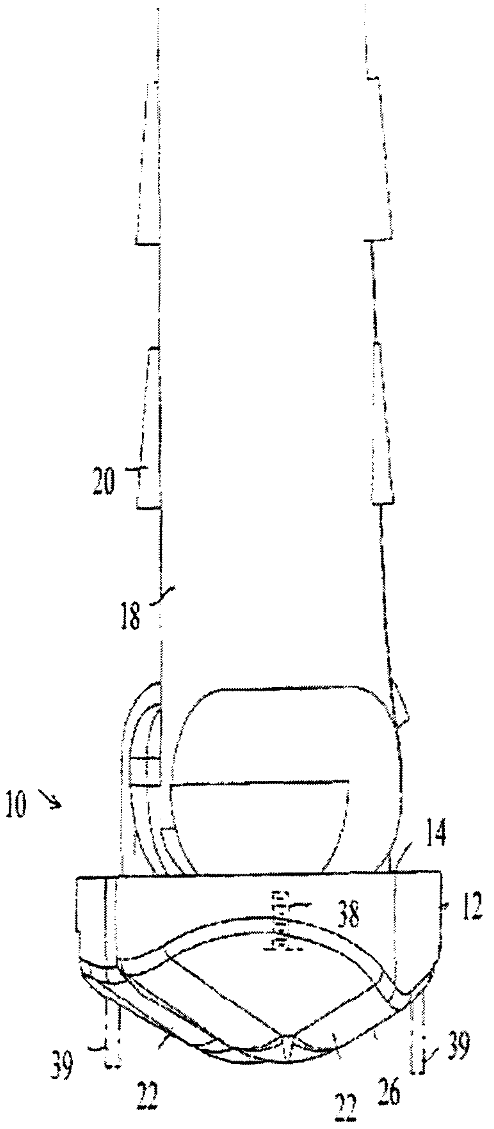

In another embodiment, a device as described herein further comprises an additional bulbous protuberance or bulbous protuberances, non-bulbous protuberance 39, or non-bulbous protuberances shown in FIG. 3. In another embodiment, protuberances 39 are formed in the shape of a peg, stud, bolt, pin, dowel and the like, although the invention is not limited to these shapes. In another embodiment, protuberances 39 may be rigid or flexible. In another embodiment, protuberances 39 are of different resilience or hardness, such as having different elasticity properties or Shore hardness. In another embodiment, protuberances 39 protrude by different amounts from the lower surface 24 of support member 12. In another embodiment, the amount of protrusion of protuberances 39 or height is adjusted. In another embodiment, protuberance 39 is fixed or movable at any place on the lower surface 24 of support member 12.

In another embodiment, a protuberance is slidingly mounted on support member 12. In another embodiment, a device such as footwear 10 comprises a sliding/shifting mechanism for a protuberance inside the sole of footwear 10. In another embodiment, the sliding/shifting mechanism comprises, without limitation, a mechanism that floats in a viscous matrix (e.g., fluid in a chamber formed in the sole), that is suspended by inner cables, or a niche trapping a protuberance with a fixing mean.

Fixing a Protuberance

Figure 2:
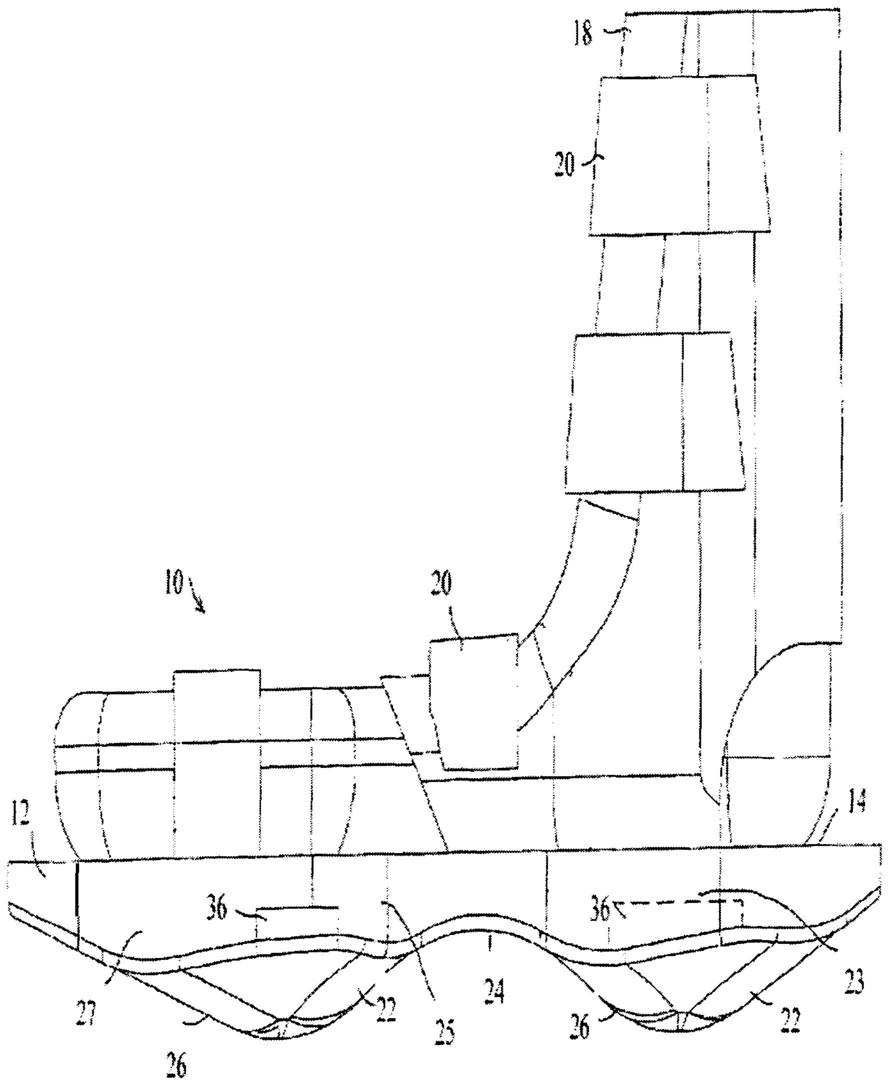
FIGS. 2 and 3 are simplified side-view and rear-view illustrations, respectively, of the footwear of FIG. 1.

As seen clearly in FIG. 2, one protuberance 22 may be positioned more posteriorly than the other protuberance 22. In another embodiment, a device as described herein comprises at least one anterior protuberance. In another embodiment, a device as described herein comprises at least one posterior protuberance. In another embodiment, the device consists of one anterior protuberance and one posterior protuberance. In another embodiment, the device comprises at least one anterior protuberance and one moveable posterior protuberance. In another embodiment, the device comprises at least one moveable anterior protuberance and one posterior protuberance. In another embodiment, the device comprises at least one moveable anterior protuberance and one moveable posterior protuberance. In another embodiment, the device consists of one moveable anterior protuberance and one moveable posterior protuberance.

In another embodiment, the protuberances rise vertically and therefore each protuberance comprises a base end and a peak end. In another embodiment, the surface area of the base is larger than the surface area of the peak. In another embodiment, the peak is the ground engaging portion of a protuberance in the stance phase. In another embodiment, the peak is the ground engaging portion of a protuberance in all gait phases.

In another embodiment, a protuberance such as a bulbous protuberance 22 protrudes from the upper surface 14 of support member 12.

Positions of the Protuberances

Reference is now made, in one embodiment, to FIGS. 1-4, which illustrate footwear 10 constructed and operative in accordance with an embodiment of the present invention. Footwear 10, in one embodiment, is supplied as one or more pairs of shoe-like devices, or alternatively, as just one of the shoe-like devices. In another embodiment, a shoe-like device comprises a shoe platform and protuberances. Footwear 10, in one embodiment, is designed to adapt on a shoe such as Footwear 10. Footwear 10, in one embodiment, is a sandal or sandal-like footwear. In another embodiment, the shoe platform is a boot. In another embodiment, the shoe platform resembles a hiking boot.

In another embodiment, the footwear 10 comprises a support member 12 having a periphery in a shape of a shoe sole with an upper surface 14. In another embodiment, the footwear 10 comprises an insole placed on top of the upper surface 14. In another embodiment, the insole is the interior bottom of footwear 10. In another embodiment, the insole sits directly beneath the foot. In another embodiment, the insole is removable, replaceable, or both. In another embodiment, the insole adds comfort, control the shape, moisture, smell, or any combination thereof. In another embodiment, the insole is placed to correct defects in the natural shape of the foot or positioning of the foot during standing or walking.

In another embodiment, a support member 12 comprises an outsole. In another embodiment, a support member 12 comprises lower surface 24 or an outsole of support member 12. In another embodiment, lower surface 24 or an outsole is made of natural rubber or a synthetic imitation. In another embodiment, lower surface 24 or an outsole comprises a single piece, or may comprise separate pieces of different materials. In another embodiment, lower surface 24 or an outsole can be softer or harder. In another embodiment, a support member 12 further comprises a midsole which is a layer in between the outsole and the insole the most pressure down. In another embodiment, a support member 12 does not have a midsole.

In another embodiment, positioning at least a first bulbous protuberance and a second bulbous protuberance in a balanced position is the position in which the footwear exerts the least valgus, varus, dorsal or plantar torque about the ankle in a subject being examined. In another embodiment, positioning at least a first bulbous protuberance and a second bulbous protuberance in a balanced position is the position in which the footwear provides the least or minimal lower limbs muscle tonus. In another embodiment, positioning at least a first bulbous protuberance and a second bulbous protuberance in a balanced position is the position in which the footwear provides balanced lower limbs muscle tonus. In another embodiment, positioning at least a first bulbous protuberance and a second bulbous protuberance in a balanced position is toning lower limb muscles. In another embodiment, positioning at least a first bulbous protuberance and a second bulbous protuberance in a balanced position is toning the amount of tension or resistance to movement in a muscle involved in gait. In another embodiment, positioning at least a first bulbous protuberance and a second bulbous protuberance in a balanced position is lower limb unloading that allows maximal ankle, knee, and hip joint mobility. In another embodiment, positioning at least a first bulbous protuberance and a second bulbous protuberance in a balanced position is providing a reduction of muscle tone, larger passive ankle excursion, improved gait ability, or any combination thereof. In another embodiment, positioning at least a first bulbous protuberance and a second bulbous protuberance in a balanced position is increasing stride length, stance symmetry, or a combination thereof. In another embodiment, positioning at least a first bulbous protuberance and a second bulbous protuberance in a balanced position is increasing the length of the force point of action in lower limb muscles such as but not limited to: soleus, tibialis posterior, and both gastrocnemius muscles. In another embodiment, positioning at least a first bulbous protuberance and a second bulbous protuberance in a balanced position is toning the plantar flexors. In another embodiment, positioning at least a first bulbous protuberance and a second bulbous protuberance in a balanced position is preventing excessive forward rotation as the body moves forward over the stationary foot. In another embodiment, positioning at least a first bulbous protuberance and a second bulbous protuberance in a balanced position is toning the push off of the heel.

Figure 4:
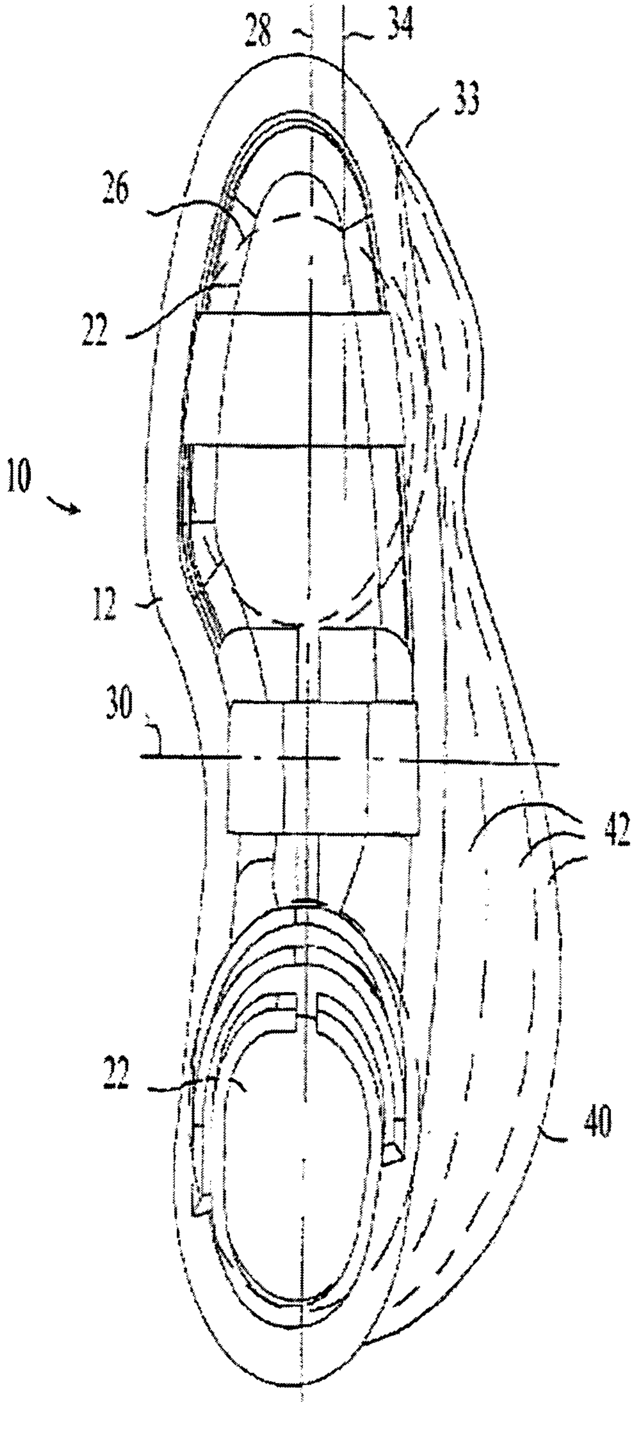
FIG. 4 is a simplified top-view illustration of the footwear of FIG. 1, showing further features of other embodiments of the present invention.

In another embodiment, as seen in FIG. 4, the protuberances are positioned on a common longitudinal axis of support member 12, such as the centerline 28 of support member 12. In another embodiment, the protuberances are positioned on opposite sides of the latitudinal midline 30. In another embodiment, the protuberances are positioned offset from the centerline 28 of support member 12, and on opposite sides of the latitudinal midline 30. In another embodiment, the bases of the protuberances are positioned on the centerline of the support member. In another embodiment, the peaks of the protuberances are positioned on opposite sides of the centerline of support member. In some embodiments, the meaning of "protuberance is positioned offset from the centerline" comprises that the peak or the ground engaging surface of a protuberances is positioned offset from the centerline. In some embodiments, the meaning of "protuberance is positioned offset from the centerline" comprises that only the peak or the ground engaging surface of a protuberances is positioned offset from the centerline but the centerline still crosses the protuberance.

In another embodiment, the peak or the ground engaging surface of the anterior protuberance is positioned laterally from the centerline of the support member. In another embodiment, the peak or the ground engaging surface of the anterior protuberance is positioned medially from the centerline of the support member. In another embodiment, the peak or the ground engaging surface of the anterior protuberance is positioned laterally from the centerline of the support member and the peak or the ground engaging surface of the posterior protuberance is aligned with centerline. In another embodiment, the peak or the ground engaging surface of the anterior protuberance is positioned medially from the centerline of the support member and the peak or the ground engaging surface of the posterior protuberance is aligned with centerline.

In another embodiment, the peak or the ground engaging surface of the posterior protuberance is positioned laterally from the centerline of the support member. In another embodiment, the peak or the ground engaging surface of the posterior protuberance is positioned medially from the centerline of the support member. In another embodiment, the peak or the ground engaging surface of the posterior protuberance is positioned laterally from the centerline of the support member and the peak or the ground engaging surface of the anterior protuberance is aligned with centerline. In another embodiment, the peak or the ground engaging surface of the posterior protuberance is positioned medially from the centerline of the support member and the peak or the ground engaging surface of the anterior protuberance is aligned with centerline.

In another embodiment, the peak or the ground engaging surface of the posterior protuberance is positioned laterally from the centerline of the support member and the peak or the ground engaging surface of the anterior protuberance is positioned medially from the centerline of the support member. In another embodiment, the peak or the ground engaging surface of the anterior protuberance is positioned laterally from the centerline of the support member and the peak or the ground engaging surface of the posterior protuberance is positioned medially from the centerline of the support member.

Figure 5:
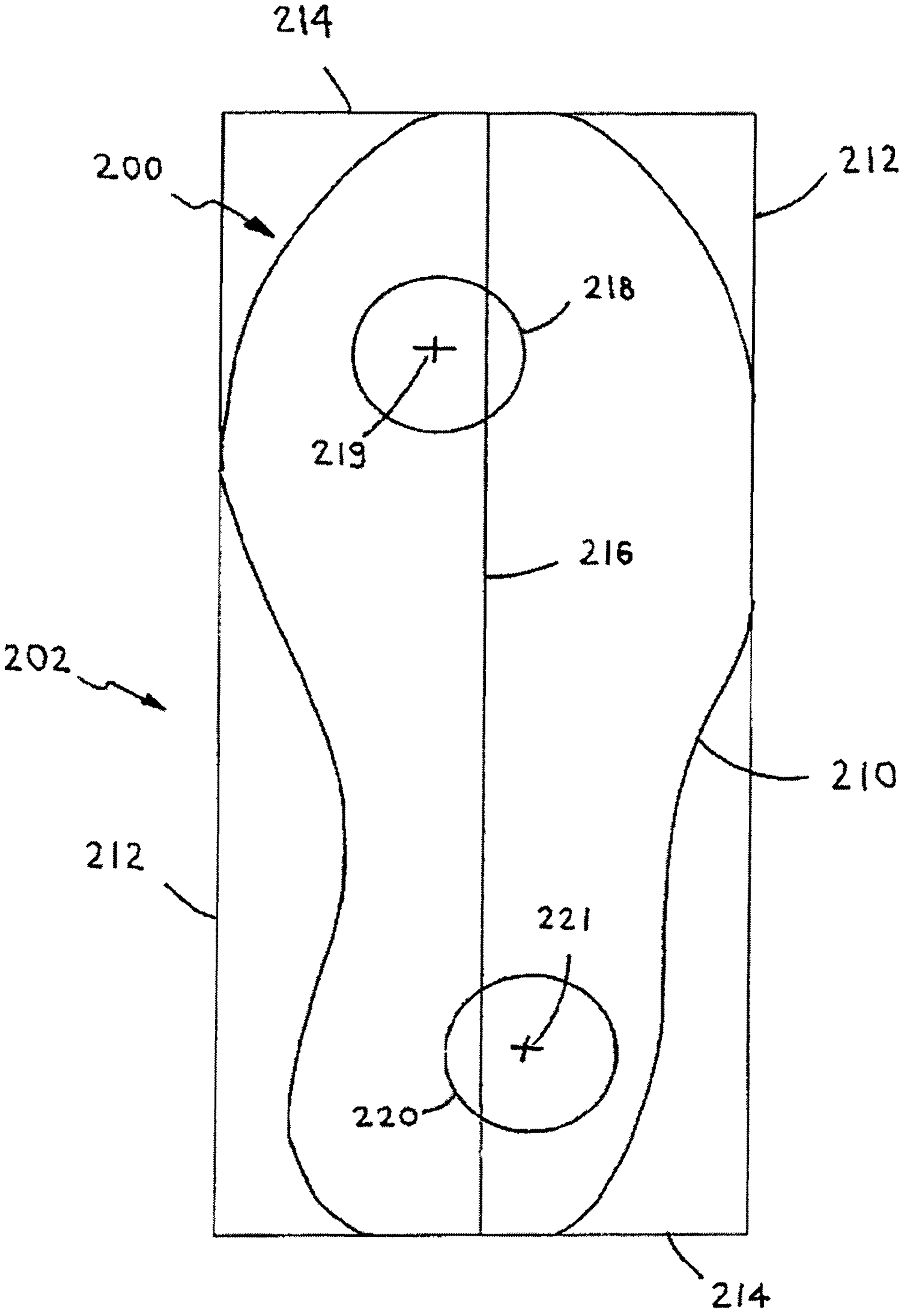
FIG. 5 is a simplified pictorial illustration of an alignment of the anterior (forward) and posterior (rearward) protuberances on a support member, according to embodiments of the present invention.
Figure 6:
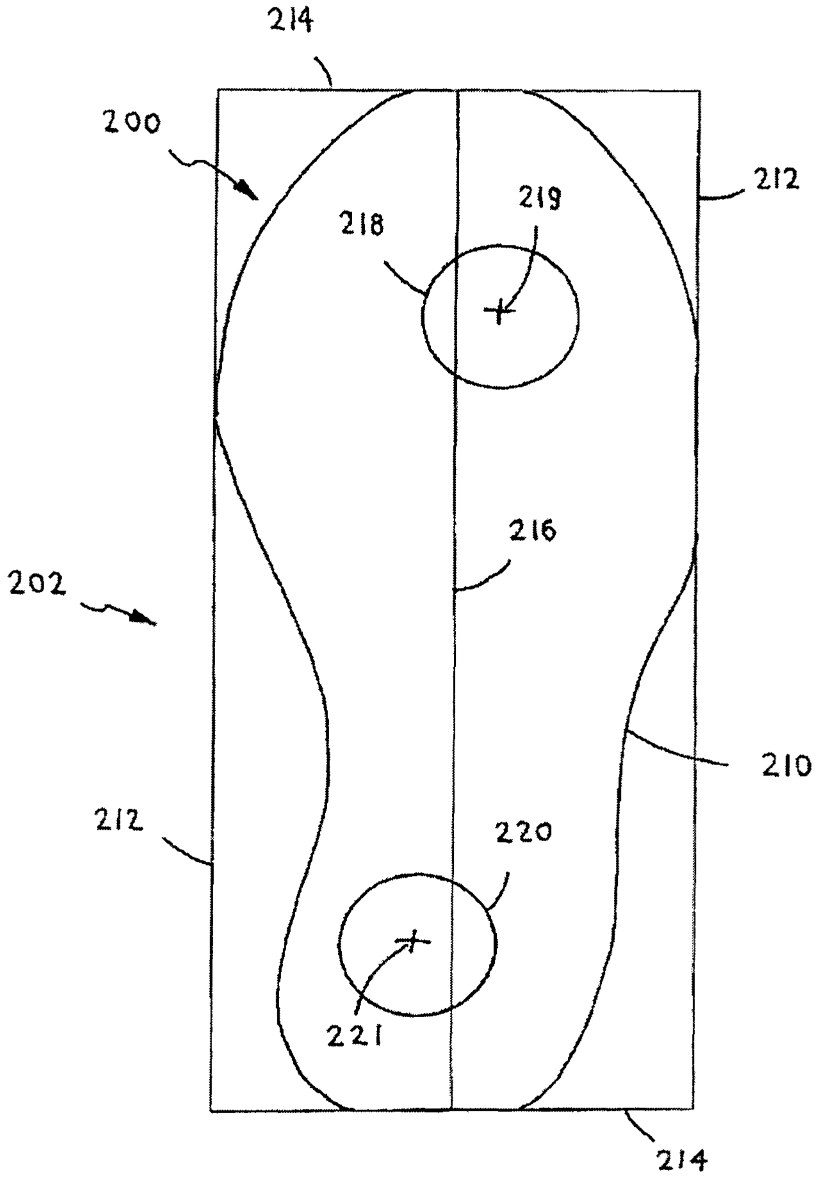
FIG. 6 is a simplified pictorial illustration of another alignment of the anterior and posterior protuberances on a support member, according to embodiments of the present invention.

In another embodiment, the centerline divides longitudinally the calcaneus support portion into two equal halves and further extends towards the phalanges and metatarsals support portion in a straight line. In another embodiment, the centerline divides longitudinally the arch of the calcaneus support portion into two equal halves and further extends towards the phalanges and metatarsals support portion in a straight line. In another embodiment, the centerline divides longitudinally the proximal arch of the calcaneus support portion into two equal halves and further extends towards the phalanges and metatarsals support portion in a straight line. In another embodiment, the centerline divides longitudinally the support portion as seen in FIGS. 5-6 of the calcaneus support portion into two equal halves and further extends towards the phalanges and metatarsals support portion in a straight line. In another embodiment of the present invention, the longitudinal centerline is defined as a longitudinal straight line connecting middles of the short sides of a rectangle which delimits a contour of the support member.

In another embodiment, the bases of the protuberances are positioned on the centerline of the support member and the peaks of the protuberances are positioned on opposite sides of the centerline of support member. In another embodiment, the bases of the protuberances are positioned on the centerline of the support member but the peaks of the protuberances are offset from the centerline of the support member. In another embodiment, the bases of the protuberances are positioned on the centerline of the support member but the peaks of the protuberances are positioned on opposite sides of the centerline of the support member. In another embodiment, positioning a protuberance is positioning the peak or the ground engaging surface of a protuberance. In another embodiment, the terms "peak" and "ground engaging surface" are used interchangeably.

In another embodiment, the anterior protuberance is positioned medially from the centerline of the support member. In another embodiment, the peak of the anterior protuberance is positioned medially from the centerline of the support member. In another embodiment, the base of the anterior protuberance is positioned on the centerline of the support member but the peak of the anterior protuberance is positioned medially from the centerline of the support member. In another embodiment, the anterior protuberance is positioned laterally from the centerline of the support member. In another embodiment, the peak of the anterior protuberance is positioned laterally from the centerline of the support member. In another embodiment, the base of the anterior protuberance is positioned on the centerline of the support member but the peak of the anterior protuberance is positioned laterally from the centerline of the support member. In another embodiment, the posterior protuberance is positioned medially from the centerline of the support member. In another embodiment, the peak of the posterior protuberance is positioned medially from the centerline of the support member. In another embodiment, the base of the posterior protuberance is position on the centerline of the support member but the peak of the posterior protuberance is positioned medially from the centerline of the support member. In another embodiment, the posterior protuberance is positioned laterally from the centerline of the support member. In another embodiment, the peak of the posterior protuberance is positioned laterally from the centerline of the support member. In another embodiment, the base of the posterior protuberance is position on the centerline of the support member but the peak of the posterior protuberance is positioned laterally from the centerline of the support member.

In another embodiment, as seen in FIG. 2, the posterior protuberance 22P is positioned generally underneath a calcaneus (heel, ankle) support portion 23 of support member 12. In another embodiment, the anterior protuberance (22A) may be positioned generally underneath a metatarsals support portion 25 and/or phalanges support portion 27 of support member 12.

In another embodiment, as indicated by broken lines 33 in FIG. 4, the anterior protuberances 22A is aligned on a longitudinal axis with its peak offset from centerline 28, and the posterior protuberance (22P) is also is aligned on a longitudinal axis with its peak offset from centerline 28 but to the opposite direction of 22A with respect to centerline 28.

In another embodiment, FIG. 5 is a simplified pictorial illustration of an alignment of the anterior (forward) and posterior (rearward) protuberances on a support member 200, according to embodiments of the present invention. Centerline 216, in the embodiment is defined as a longitudinal straight line (median) that connects the middles of short sides 214 of a rectangle 212, the long sides 212 of which are parallel to centerline 216, and which delimits the contour 210 of the support member. In embodiments of the present invention contour 210 is the contour (254, see FIG. 7) of the foothold confined by the upper part (253, see FIG. 7) of the footwear (250, see FIG. 7), corresponding to the last which is used to form the footwear. In other embodiments of the present invention contour 210 is the outermost contour of the footwear. In other embodiments of the present invention contour 210 is the contour of the bottom surface of the sole of the footwear. In some embodiments, the terms "forward" and "anterior" are used interchangeably. In some embodiments, the terms "rearward" and "posterior" are used interchangeably.

According to embodiments of the present invention, as shown in FIG. 5, forward protuberance 218 at the anterior (phalanges) portion of the support member (i.e. its front portion) is positioned medially offset to centerline 216. By "medially offset" is meant that a peak surface (which can be the ground engaging surface) of protuberance 218 (marked by cross 219) is shifted from centerline 216 medially towards the inner side of support surface 200, facing the support member of the other foot (not shown in this figure). The peak surface is a surface on the protuberance which is furthest from the support surface with respect to other surfaces of the protuberance.

According to embodiments of the present invention, as shown in FIG. 5, rearward (posterior) protuberance 220 at the posterior (calcaneus) portion of the support member (i.e. its back portion) is positioned laterally offset to centerline 216. By "laterally offset" is meant that a peak surface (which can be the ground engaging surface) of protuberance 220 (marked by cross 221) is shifted from centerline 216 laterally towards the outer side of support surface 200, away from the support member of the other foot (not shown in this figure).

The alignment of the protuberances shown in FIGS. 5 and 6 is useful, for example, for tuning pelvic muscles.

FIG. 6 is a simplified pictorial illustration of another alignment of the anterior and posterior protuberances on a support member, according to embodiments of the present invention. According to embodiments of the present invention, as shown in FIG. 6, forward (anterior) protuberance 218 is laterally offset to centerline 216, whereas rearward protuberance 220 is medially offset to centerline 216.

Figure 7:
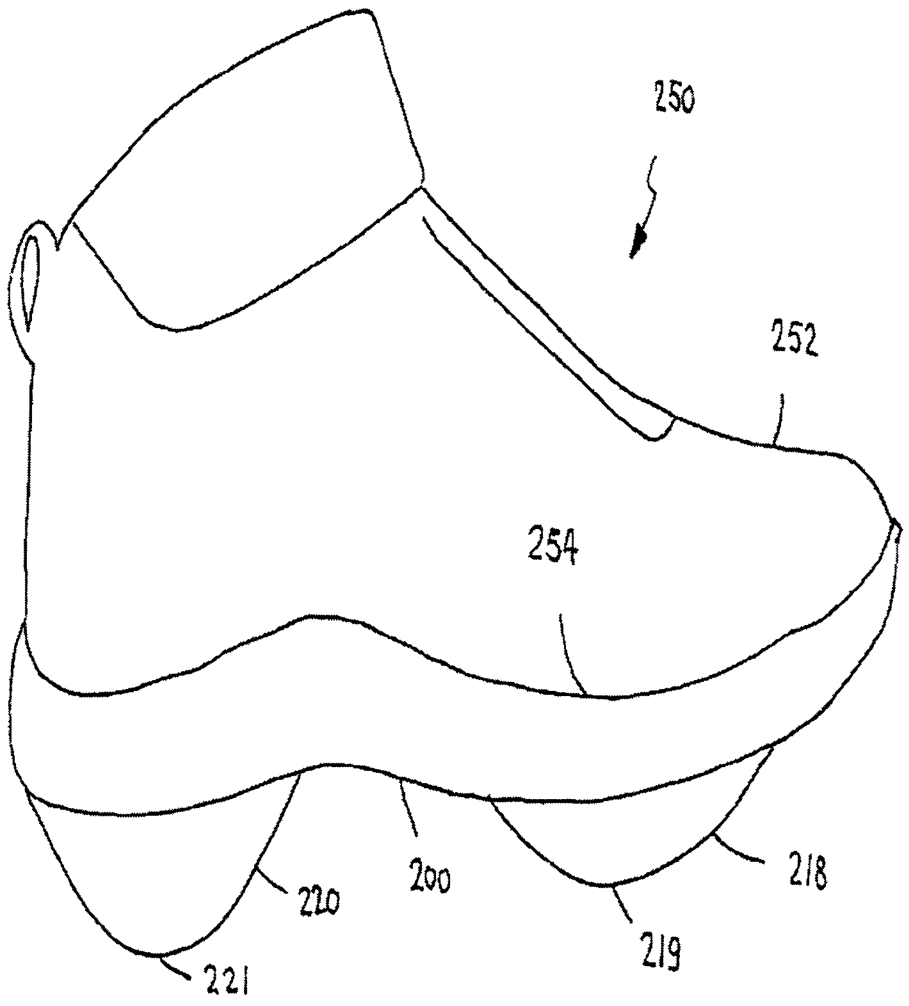
FIG. 7 is a simplified pictorial illustration of a sneaker constructed and operative in accordance with an embodiment of the present invention, whose rearward protuberance has a greater height than the height of the forward protuberance.

FIG. 7 is a simplified pictorial illustration of a sneaker 250 constructed and operative in accordance with an embodiment of the present invention, whose rearward protuberance 220 has a greater height than the height of the forward protuberance 218. It is noticeable that such arrangement facilitates initial contact between rearward protuberance 220 and the supporting ground (not shown in this figure) when a user wears the sneaker, before the forward protuberance is brought in contact with the ground. When both protuberances are placed in contact with the ground the foot of the user wearing sneaker 250 acquires a downward inclination with respect to direction of gait of the user.

Figure 8:
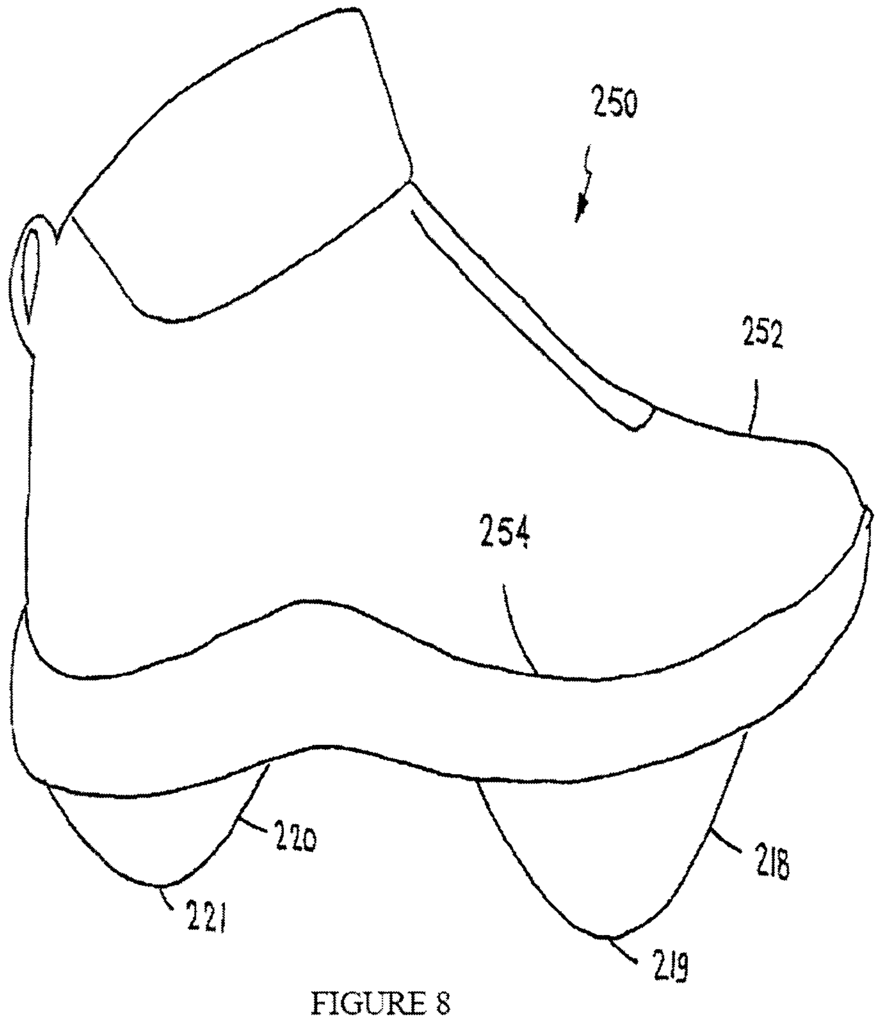
FIG. 8 is a simplified pictorial illustration of a sneaker constructed and operative in accordance with an embodiment of the present invention, whose forward protuberance has a greater height than the height of the rearward protuberance.

FIG. 8 is a simplified pictorial illustration of a sneaker 250 constructed and operative in accordance with an embodiment of the present invention, whose forward protuberance 218 has a greater height than the height of the rearward protuberance 220. In this embodiment when both protuberances are placed in contact with the ground the foot of the user wearing sneaker 250 acquires an upward inclination (with respect to the direction of gait of the user.

Figure 9:
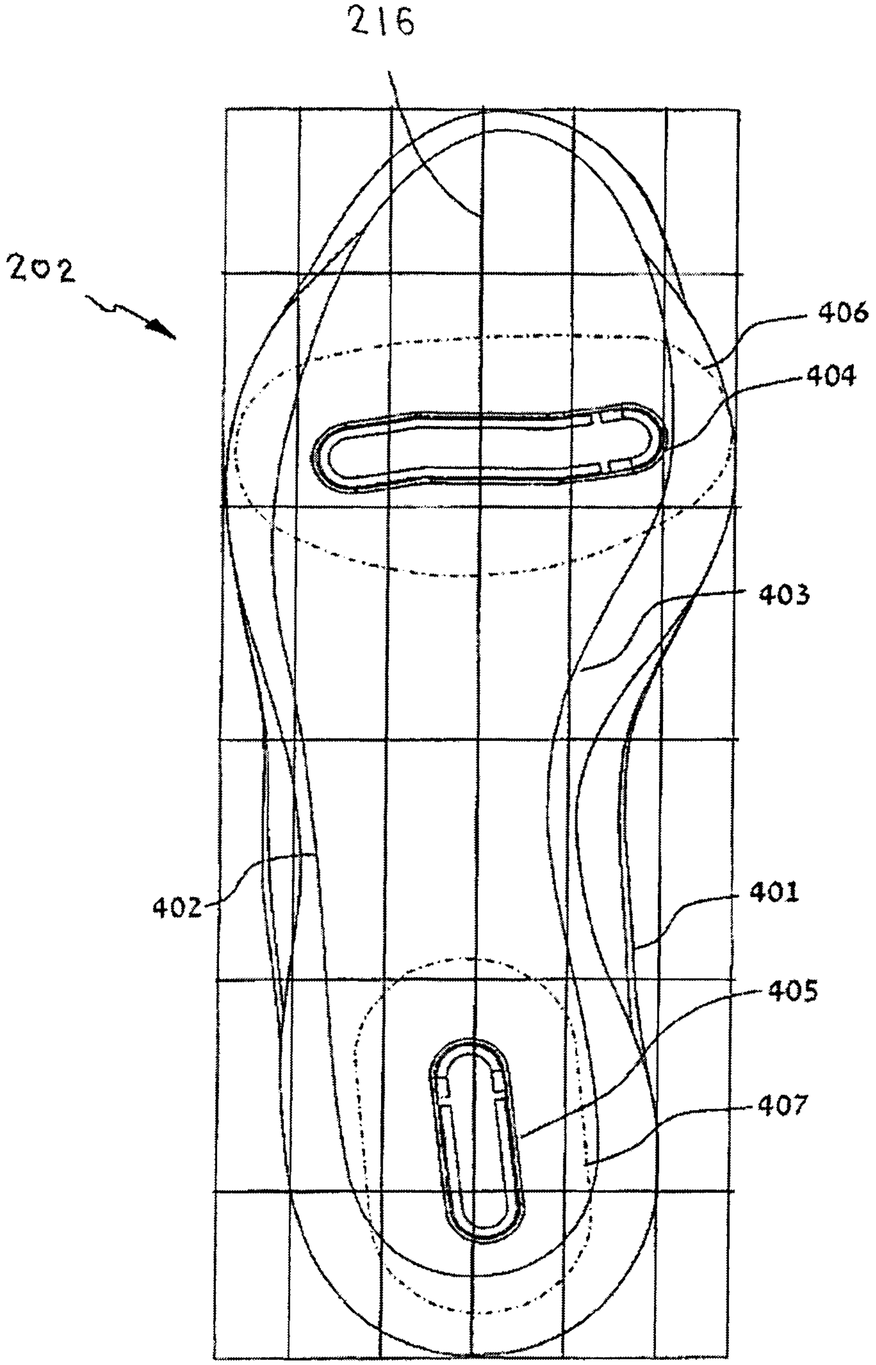
FIG. 9 illustrates maximal area boundaries of positioning of the anterior and posterior protuberances with respect to a support surface, according to embodiments of the present invention.

FIG. 9 illustrates maximal area boundaries of positioning of the anterior and posterior protuberances with respect to a support surface, according to embodiments of the present invention. Shown in this figure is a bottom view of a sneaker designed to be worn on a right foot of a user. The medial side is thus the right side of the drawing, facing the arc of greater curvature of the side arcs of the sneaker. The lateral side is opposite to the medial side that is the left side of the drawing, facing the arc of lesser curvature of the side arcs of the sneaker. Indicated are the midsole 401 and last/shoe 402, contour 403 of the foothold which is determined by the last used in the making of the sneaker. Front rail 404 and rear rail 405 are used for anchoring the protuberance. The area bordered by dotted line 406 marks the maximal area within which the peak surface of the anterior protuberance, i.e. the ground engaging surface of the anterior protuberance, may be located, according to some embodiments of the present invention. The area bordered by dotted line 407 marks the maximal area within which the peak surface of the posterior protuberance.

Figure 10:
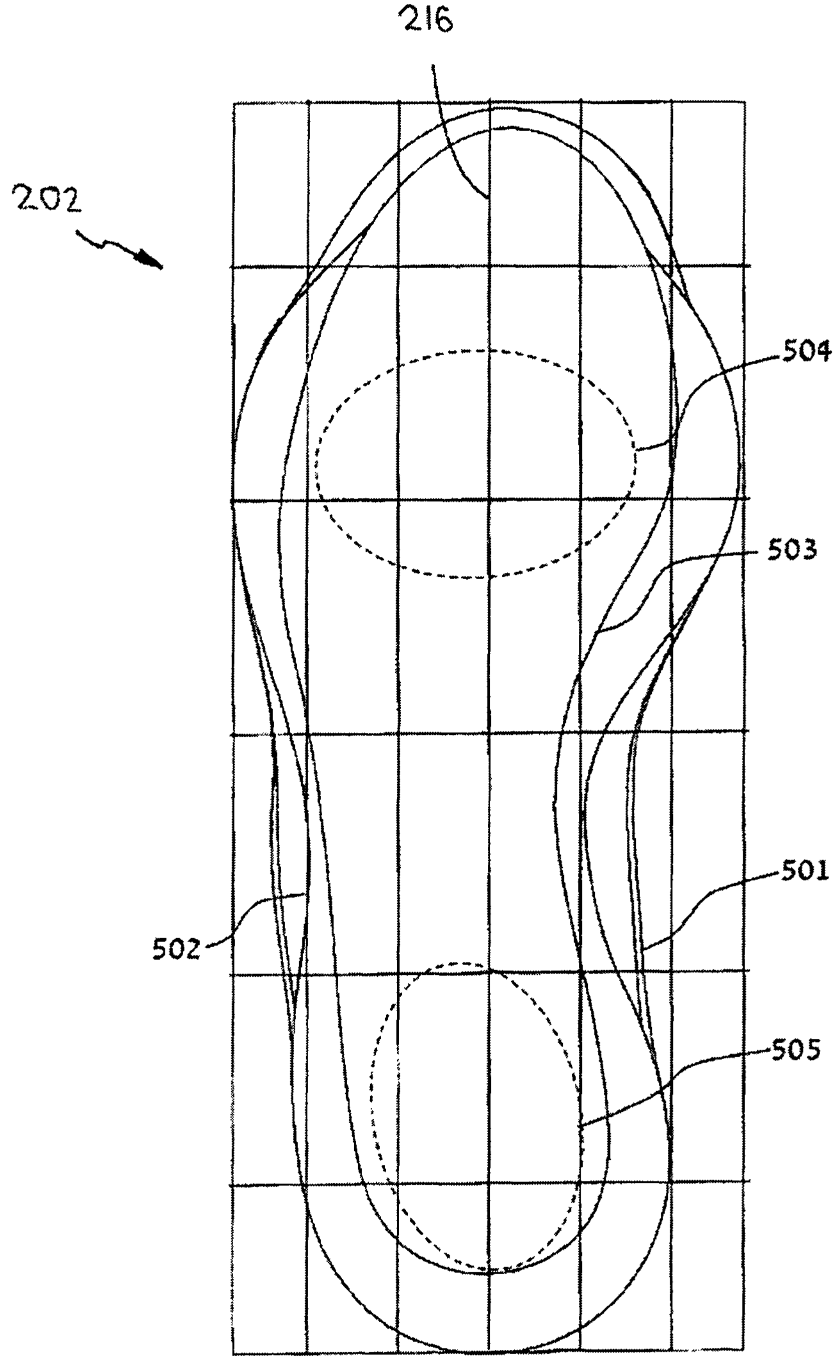
FIG. 10 illustrates effective area boundaries of positioning of the anterior and posterior protuberances with respect to a support surface, according to embodiments of the present invention.

FIG. 10 illustrates the effective area boundaries of positioning of the anterior and posterior protuberances with respect to a support surface, according to embodiments of the present invention. Indicated are the midsole 501 and outsole 502, contour 503 of the foothold which is determined by the last used in the making of the sneaker. The area bordered by dotted line 504 marks the effective area within which the peak surface of the anterior protuberance, i.e. the ground engaging surface of the anterior protuberance, may be located, according to some embodiments of the present invention. The area bordered by dotted line 505 marks the effective area within which the peak surface of the posterior protuberance. "Effective" refers to the effectiveness of use of the footwear according to embodiments of the present invention, which facilitates treatment. For clarity both FIGS. 9 and 10 are divided to 36 equal parts. The effective locations will be within the same parts regardless of sizing.

Figure 11A:
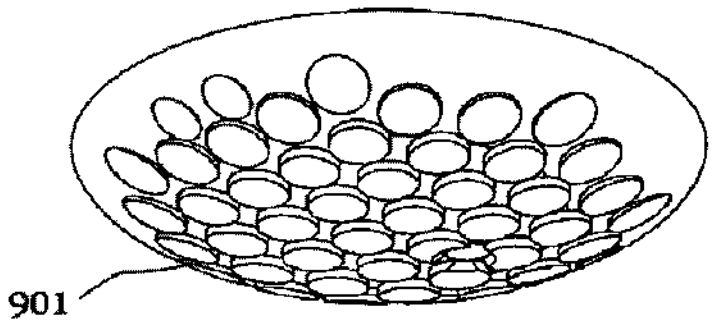
FIG. 11A is an isometric view of a protuberance suitable for use on a footwear, according to embodiments of the present invention.
Figure 11B:
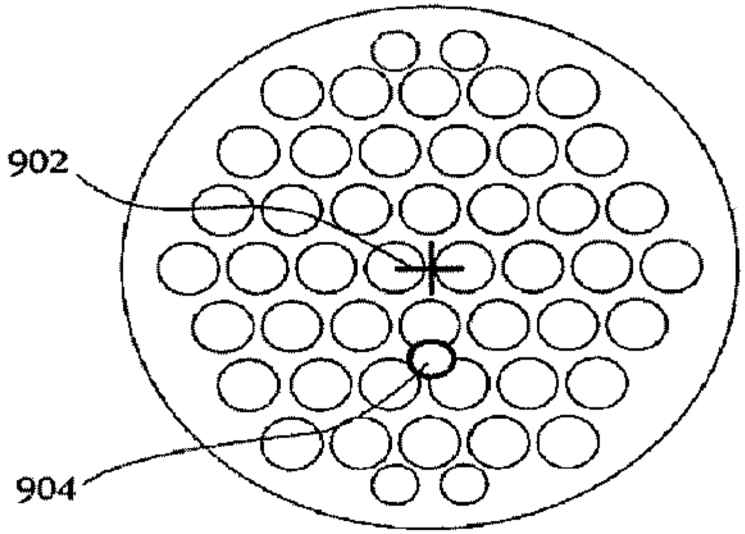
FIG. 11B is a frontal view of a protuberance suitable for use on a footwear, according to embodiments of the present invention.
Figure 11C:
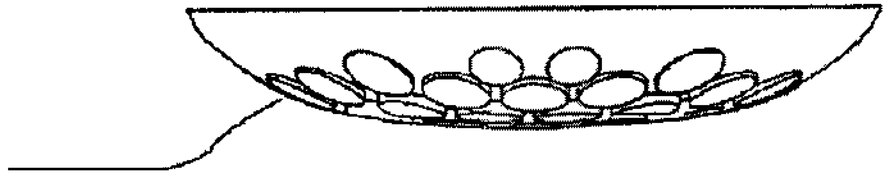
FIG. 11C is a side view of a protuberance suitable for use on a footwear, according to embodiments of the present invention.

FIG. 11A is an isometric view of a protuberance suitable for use on a footwear, according to embodiments of the present invention. Cleats 901, according to embodiments of the present invention, cover the ground engaging area of a protuberance, for facilitating enhanced grip of the surface on which the user stands or walks. FIG. 11B is a frontal view of a protuberance suitable for use on a footwear, according to embodiments of the present invention. The peak surface is marked by cross 902. Bore 904 is provided for a screw or other fastening arrangement to fix the protuberance in the desired position. FIG. 11C is a side view of a protuberance suitable for use on a footwear, according to embodiments of the present invention. Convexity 905 of the protuberance is clearly seen. Various convexities may be employed, all of which define a peak surface, typically (but not necessarily) at the center of the protuberance, which is the surface which comes in contact with the ground, when the user attaches the support member to the foot, and walks or stands on the ground.

FIG. 11 is a simplified pictorial illustration of a protuberance according to embodiments of the present invention. As shown a protuberance is convex 905 (11C). Each protuberance, according to embodiments of the present invention, comprises a fixing hole (for fixing a protuberance) 904 in which a latch, a bolt, or a screw is placed therein. The peak of a protuberance, which in some embodiments of the present invention, is placed within the center of the ground engaging area 902 is in contact with the ground during stance (11B). A grip structure 901.

Resilience, Hardness, and Elasticity

In another embodiment, calibrating comprises positioning a protuberance on a support member. In another embodiment, calibrating comprises adjusting the height or protrusion of a protuberance. In another embodiment, calibrating comprises adjusting a resilience of a protuberance. In another embodiment, calibrating comprises adjusting a hardness of a protuberance. In another embodiment, calibrating comprises adjusting an elasticity of a protuberance.

In another embodiment, a protuberance is compressible. In another embodiment, a protuberance is deformable. In another embodiment, a protuberance is compressible or deformable upon pressure exerted by subject's weight.

In another embodiment, a protuberance is constructed of any suitable material, such as but not limited to, elastomers or metal or a combination of materials, and have different properties. In another embodiment, a protuberance comprises different resilience or hardness, such as having different elasticity properties or Shore hardness.

In another embodiment, a protuberance comprises spikes or grip means for providing better stability. In another embodiment, a protuberance comprises spikes or grip means as anti-slippery means. In another embodiment, FIG. 11 provides a protuberance comprising small rounded grip means. In another embodiment, spikes or grip means are constructed of any suitable material, such as but not limited to: elastomers such as rubbers or plastic materials. In another embodiment, spikes or grip means cover only a portion of a protuberance. In another embodiment, spikes or grip means cover at least a ground engaging surface of a protuberance (the surface in contact with the ground during stance). In another embodiment, a fixing means for securing a protuberance to the support portion is embedded within a spikes or a grip means. In another embodiment, a fixing means for securing a protuberance to the support portion is places in between spikes or a grip means.

In another embodiment, a protuberance has a shore hardness of between 30 to 90 Sh A. In another embodiment, a protuberance has a shore hardness of between 40 to 55 Sh A. In another embodiment, a protuberance has a shore hardness of between 50 to 70 Sh A. In another embodiment, a protuberance has a shore hardness of between 65 to 90 Sh A. In another embodiment, a protuberance has a shore hardness of between 55 to 60 Sh A. In another embodiment, a protuberance has a shore hardness of between 65 to 70 Sh A. In another embodiment, an anterior and a posterior protuberance comprise identical shore hardness. In another embodiment, an anterior and a posterior protuberance comprise different shore hardness.

In another embodiment, a protuberance is a soft protuberance comprising a shore hardness of between 40 to 55 Sh A. In another embodiment, a protuberance is a medium hardness protuberance comprising a shore hardness of between 50 to 70 Sh A. In another embodiment, a protuberance is a hard protuberance comprising a shore hardness of between 65 to 90 Sh A.

In another embodiment, a protuberance has an abrasion between 1-60 $mm^3$ (by DIN 53516). In another embodiment, a protuberance comprises a rubber cup. In another embodiment, a protuberance comprises natural rubber compounds. In another embodiment, a protuberance comprises synthetic rubber compounds such as TPU or TPR. In another embodiment, a protuberance comprises silicone. In another embodiment, a protuberance a plastic material such as PA 6 (nylon), PA6/6 (nylon)+glass fiber, ABS, Polypropylene, POM (Polyoxymethylene). In another embodiment, a protuberance comprises a metal such as aluminum, steel, stainless steel, brass, or metal alloys. In another embodiment, a protuberance comprises compound materials such as glass fibers, carbon fibers, aramid fibers (e.g., Kevlar®), or any combination thereof.

Adjustments

In another embodiment, different heights of a protuberance can be used. In another embodiment, height is calibrated by adding a spacer between a protuberance and the outsole. In another embodiment, different weights of a protuberance can be used. In another embodiment, weight is calibrated by adding a weighted spacer between a protuberance and the outsole.

In another embodiment, the height of the anterior protuberance differs from the height of the posterior protuberance.

In another embodiment, the height of the anterior protuberance or of the posterior protuberance is adjusted with round spacers positioned between the support member or the outsole and the base portion of a protuberance. In another embodiment, a spacer is fixed between the outsole and base portion of a protuberance.

In another embodiment, a spacer or a protuberance comprises a diameter of 50-150 mm. In another embodiment, a spacer or a protuberance comprises a diameter of 55-110 mm. In another embodiment, a spacer or a protuberance comprises a diameter of 60-100 mm. In another embodiment, a spacer or a protuberance comprises a diameter of 80-90 mm. In another embodiment, a spacer or a protuberance comprises a diameter of 85 mm. In another embodiment, a spacer or a protuberance or a protuberance comprises a thickness of 1-12 mm. In another embodiment, a spacer or a protuberance comprises a thickness of 1-4 mm. In another embodiment, a spacer or a protuberance comprises a thickness of 3-10 mm. In another embodiment, a spacer or a protuberance comprises a thickness of 1-3 mm. In another embodiment, a spacer or a protuberance comprises hardness of 60-70 Shore A, which is a soft spacer. In another embodiment, a spacer or a protuberance comprises hardness of 90-100 Shore A, which is a hard spacer. In another embodiment, a spacer or a protuberance comprises hardness of 71-890 Shore A, which is medium hardness spacer.

In another embodiment, a spacer or a protuberance weighs 2-500 g. In another embodiment, a spacer or a protuberance weighs 2-250 g. In another embodiment, a spacer or a protuberance weighs 2-6 g. In another embodiment, a spacer or a protuberance weighs 2-20 g. In another embodiment, a spacer or a protuberance weighs 2-20 g is made of Nylon. In another embodiment, a spacer or a protuberance weighs 2-20 g is made of Nylon and fiber. In another embodiment, a spacer or a protuberance weighs 2-40 g is made of Nylon and glass fiber. In another embodiment, a spacer or a protuberance weighs 30-100 g. In another embodiment, a spacer or a protuberance weighs 50-80 g. In another embodiment, a spacer or a protuberance weighs 60-100 g. In another embodiment, a spacer or a protuberance comprises: Nylon glass fiber polyurethane an alloy (such as but not limited to Zink alloy), or any combination thereof.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Materials and Methods

Positioning Method

After each change (calibration, positioning) in configuration in the protuberances attached to the footwear, the patient was asked to walk a distance of 10 meters away from the therapist and then back in order to verify that the patient remains balanced and that the change in configuration resulted in a desired positive effect.

Prescribing the Device

The device comprises 2 units of footwear: one for the left foot and one to the right foot. The footwear used is a light walking boot.

Prescription included a set of instructions to the patients. These instructions included: the length of wear the device per day (usually 30-60 minutes daily). Daily use included wearing the device during routine activities that may include watching TV, computer activities; eating activities, etc. Actual walking constituted 10-25% of 30-60 minutes. Thus, if the patient has worn the device for 60 minutes per day, total of 5-10 minutes were dedicated, accumulatively, to walking.

Example 1

Treating Urinary Incontinence

A 74 years old woman is presented to the treatment center with a main complaint of urinary incontinence during physical efforts.

Case History: The woman reported that incontinence started after the birth of her third son, and worsened after each birth (she had 5 vaginal births). She reported that for the last 4 years she uses pads since whenever she coughs sneezes or lifts a heavy object she faces uncontrolled urination (urine leaks). A written evaluation from an urologist specializing in incontinence described a positive stress test.

Questionnaires: I-QOL score was 62 at baseline.

Therapy

Bulbous protuberances with B convexity and “soft” resilience were connected and fixed under the hind-foot and forefoot of the left and right footwear.

Balancing: The device was calibrated and fine tuned during repeated clinical gait assessments while the patient is wearing the device. During this process care is taken to reduce the eversion and inversion during heel strike, loading response, mid-stance and toe-off.

Heel-Rise Timing: The patient was asked to walk 20 m in order to confirm that she is still balanced and the heel-rise is well timed in the gait cycle. There were no abnormalities observed in heel-rise timing.

Treatment Plan: The patient was briefed with safety instructions and was asked to wear the system at home for 45 minutes a day on each day of the first week of the treatment. During this time she was instructed to be seated for most (80%) of the time, getting up occasionally to do daily activities such as answering the phone or getting a drink. Accumulative weight bearing time per day in the first week was 7 to 9 minutes (20% of total time with the system). The patient was instructed to increase the total wearing time by 15 minutes per week maintaining an accumulative 20% of weight bearing time with the device. The patient was seen for follow-up consultations at the center 4 weeks after her first visit, 10 weeks after her first visit, and 5 months after his first visit.

Treatment Progression: In the first follow up consultation the patient reported that she felt more comfortable performing indoors daily activities with the device than with her regular shoes. She reported that she found she did not have to get to the toilet quickly whenever she felt the need to urinate. Her I-QOL score was 74. She was then asked to increase the total wearing time of the system by 15 minutes per week and maintain the 20% accumulative weight bearing time. In the second follow up consultation the patient reached a total weight bearing time of 3 hours. She reported that she had significantly less episodes of incontinence when performing physical tasks such as lifting. Her I-QOL score further increased to 88. Her gait was clinically assessed and she seemed very well balanced. Her system was therefore calibrated so that the convexity of the anterior and the posterior right and left bulbous protuberances were increased to C level of convexity. She was asked to maintain the three hours of total wearing time for two weeks and then gradually increase the total wearing time up to 5 hours. She was also instructed not to limit her indoor activities while wearing the system, so that weight bearing time would potentially be more than 20%.

In the third follow up consultation she reported she has ceased to use pads for incontinence. She was wearing the system for 5 hours daily during indoor activities and reported she found it very comfortable. Her I-QOL score reached 96.

Example 2

Urinary Urgency, Frequency, and Incontinence in a Male Patient

A 68 years old man is presented to the treatment center with a main complaint of increased urinary frequency and urgency.

Case History: The patient reports that he was diagnosed with a benign enlargement of the prostate 2 years ago. Since then he has an increased frequency in the need to urinate and reports that if he does not get to the toilet quickly he is incontinent.

Questionnaires: I-QOL score was 75 at baseline.

Therapy

Bulbous protuberances with B convexity and "soft" resilience were connected and fixed under the hind-foot and forefoot of the left and right footwear.

Balancing: The patients system was calibrated and fine tuned during repeated clinical gait assessments with the device. During this process care is taken to reduce the eversion and inversion during heel strike, loading response, midstance and toe-off.

Heel-Rise Timing: The patient was asked to walk 20 m in order to confirm that he is still balanced and the heel-rise is well timed in the gait cycle. A bilateral early heel-rise was observed. In order to correct this, a 2 mm hard spacer was fixed between the left posterior bulbous protuberance and the outsole of the left shoe in order to bring the left foot to a slight plantar-flexion, thus bringing the left foot into a more plantar flexed position. The patient was reassessed walking with the system and it was noted that the timing of the left heel-rise was normalized. At this phase a 2 mm hard spacer was placed between the right posterior bulbous protuberance and the outsole of the right shoe in order to bring the right foot to a slightly more plantar-flexed position. The patient was observed walking with the device and the timing of the right heel-rise was noted to be normalized as well.

Treatment Plan: The patient was briefed with safety instructions and was asked to wear the device at home for 45 minutes a day on each day of the first week of the treatment. During this time he was instructed to be seated for most (75%) of the time, getting up occasionally to do daily activities such as answering the phone or getting a drink. Accumulative weight bearing time per day in the first week was 9 to 12 minutes (25% of total time with the system). The patient was instructed to increase the total wearing time by 15 minutes per week maintaining an accumulative 25% of weight bearing time with the device. The patient was seen for follow-up consultations at the center 5 weeks after his first visit, 10 weeks after his first visit, and 6 months after his first visit.

Treatment Progression: In the first follow up consultation the patient reported that he felt comfortable performing indoors daily activities with the system. He reported the urgency to urinate reduced. His I-QOL score improved to 81. He was then asked to increase the total wearing time of the system by 15 minutes per week and maintain the 25% accumulative weight bearing time. In the second follow up consultation the patient has reached a total weight bearing time of 3.5 hours. He reported that he had significantly less episodes of incontinence and frequent urination and was able to restrain himself for longer periods of time. His I-QOL score further improved to 90. His gait was clinically assessed and it was found that he was very well balanced. The device was therefore calibrated so that the convexity of the anterior and the posterior right and left bulbous protuberances was increased to C level of convexity. He was asked to maintain the three hours of total wearing time for two weeks and then begin walking outside for 10 minutes in addition to the indoors wearing time. He was asked to increase outside walking by 5 minutes each week to a maximum of 40 minutes.

In the third follow up consultation he reported another substantial decrease in urinary urgency and incontinence. He was wearing the system for 3 to 4 hours a day during indoor activities and walked outside for approximately 35 minutes a day while wearing the system. His I-QOL score was 100. He was asked to continue using the system and return for a follow up consultation in six months time.

These examples present the unexpected benefit of the device in treating urinary incontinence and frequent/urgent urination.

What is claimed is:

1. A method of treating a subject suffering from urinary incontinence comprising the steps of:

(a) securing a device to a subject's foot, whereby said device comprises a foot securing mean, a support member operably attached to said securing mean, and a moveable anterior protuberance and a moveable posterior protuberance, said anterior protuberance and said posterior protuberance are ground engaging;

(b) calibrating said posterior protuberance and said anterior protuberance to:

(1) a balanced position, said balanced position comprises a position whereby said device provides a reduced inversion, a reduced eversion, or both to said subject's foot during stance phases; and (2) balanced timing of heel rise; and (c) fixing said posterior protuberance and said anterior protuberance to said support member thereby treating a subject suffering from urinary incontinence.

2. The method of claim 1, whereby said calibrating comprises adjusting:

(a) a resilience of said anterior protuberance, said posterior protuberance, or a combination thereof;

(b) a hardness of said anterior protuberance, said posterior protuberance, or a combination thereof;

(c) an elasticity of said anterior protuberance, said posterior protuberance, or a combination thereof; or (d) any combination of (a), (b), and (c).

3. The method of claim 1, whereby said calibrating comprises adjusting:

(a) a height of said anterior protuberance, said posterior protuberance, or a combination thereof;

(b) a convexity of said anterior protuberance, said posterior protuberance, or a combination thereof;

(c) a weight of said anterior protuberance, said posterior protuberance, or a combination thereof; or (d) a combination of (a), (b), and (c).

4. The method of claim 1, whereby said balanced position further comprises a position whereby minimal valgus, varus, dorsal or plantar torque about the ankle is exerted by said device on said subject's foot.

5. The method of claim 1, whereby said posterior protuberance is a bulbous protuberance, said anterior protuberance is a bulbous protuberance, or both said posterior protuberance and said anterior protuberance are bulbous protuberances.

6. The method of claim 1, whereby said posterior protuberance and said anterior protuberance are moveably mounted to said support member.

7. The method of claim 1, whereby said posterior protuberance is movable within a calcaneus support portion of said support member.

8. The method of claim 1, whereby said anterior protuberance is movable within phalanges or metatarsals support portion of said support member.

9. The method of claim 1, whereby said anterior protuberance, said posterior protuberance, or their combination comprise a cross-section with a shape of a conic section, said conic section comprising at least one of a circle, ellipse, parabola and hyperbola.

10. The method of claim 1, whereby said anterior protuberance is shaped differently from said posterior protuberance.

11. A method of reducing urinary urgency, high urinary frequency, urinary incontinence or a combination thereof in a subject in need thereof comprising the steps of:

(a) securing a device to a subject's foot, whereby said device comprises a foot securing mean, a support member operably attached to said securing mean, and a moveable anterior protuberance and a moveable posterior protuberance, said anterior protuberance and said posterior protuberance are ground engaging;

(b) calibrating said posterior protuberance and said anterior protuberance to:

(1) a balanced position, said balanced position comprises a position whereby said device provides a reduced inversion, a reduced eversion, or both to said subject's foot during stance phases; and (2) balanced timing of heel rise; and (c) fixing said posterior protuberance and said anterior protuberance to said support member thereby reducing urinary urgency, high urinary frequency, urinary incontinence or a combination thereof in a subject in need thereof.

12. The method of claim 11, whereby said calibrating comprises adjusting:

(a) a resilience of said anterior protuberance, said posterior protuberance, or a combination thereof;

(b) a hardness of said anterior protuberance, said posterior protuberance, or a combination thereof;

(c) an elasticity of said anterior protuberance, said posterior protuberance, or a combination thereof; or (d) any combination of (a), (b), and (c).

13. The method of claim 11, whereby said calibrating comprises adjusting:

(a) a height of said anterior protuberance, said posterior protuberance, or a combination thereof;

(b) a convexity of said anterior protuberance, said posterior protuberance, or a combination thereof;

(c) a weight of said anterior protuberance, said posterior protuberance, or a combination thereof; or (d) a combination of (a), (b), and (c).

14. The method of claim 11, whereby said balanced position further comprises a position whereby minimal valgus, varus, dorsal or plantar torque about the ankle is exerted by said device on said subject's foot.

15. The method of claim 11, whereby said posterior protuberance is a bulbous protuberance, said anterior protuberance is a bulbous protuberance, or both said posterior protuberance and said anterior protuberance are bulbous protuberances.

16. The method of claim 11, whereby said posterior protuberance and said anterior protuberance are moveably mounted to said support member.

17. The method of claim 11, whereby said posterior protuberance is movable within a calcaneus support portion of said support member.

18. The method of claim 11, whereby said anterior protuberance is movable within phalanges or metatarsals support portion of said support member.

19. The method of claim 11, whereby said anterior protuberance, said posterior protuberance, or their combination comprise a cross-section with a shape of a conic section, said conic section comprising at least one of a circle, ellipse, parabola and hyperbola.

20. The method of claim 11, whereby said anterior protuberance is shaped differently from said posterior protuberance.

* * * * *